United States Patent [19]

Moore et al.

[11] Patent Number: 5,014,290

[45] Date of Patent: May 7, 1991

[54] METHOD AND APPARATUS FOR GENERATING RADIATION BLOCKERS

[76] Inventors: Robert M. Moore, 100 Twin Lake La., Richmond, Va. 23229; Robert L. Smith, 9900 Lumlay Rd., Richmond, Va. 23236

[21] Appl. No.: 264,112

[22] Filed: Oct. 28, 1988

[51] Int. Cl.⁵ .......................... G21K 1/00; G21K 3/00
[52] U.S. Cl. .................................. 378/145; 378/158; 378/4; 378/62; 378/99
[58] Field of Search .................... 378/18, 62, 99, 158, 378/4, 145

[56] References Cited

U.S. PATENT DOCUMENTS

| | | | |
|---|---|---|---|
| 3,755,672 | 8/1973 | Edholm et al. | 378/158 |
| 4,109,148 | 8/1978 | Jaulmes | 250/321 |
| 4,137,454 | 1/1979 | Brandon, Jr. | 378/99 |
| 4,146,794 | 3/1979 | Duinker | 250/445 |
| 4,168,435 | 9/1979 | Duinker | 250/445 |
| 4,266,136 | 5/1981 | Duinker | 250/445 |
| 4,436,684 | 3/1984 | White | 264/138 |
| 4,442,538 | 4/1984 | Haendle | 378/99 |
| 4,609,940 | 9/1986 | Born et al. | 378/99 |
| 4,613,983 | 9/1986 | Yedid et al. | 378/99 |
| 4,628,357 | 12/1986 | Fenster | 378/99 |
| 4,674,108 | 6/1987 | Asahina et al. | 378/99 |
| 4,831,645 | 5/1989 | Guenther et al. | 378/205 |

FOREIGN PATENT DOCUMENTS 1530621 11/1978 United Kingdom .
1579265 11/1980 United Kingdom .

OTHER PUBLICATIONS

Varian Ximatron 5 Radiotherapy Simulator—brochure—Apr. 1985.
Diacor Portalcast Block Casting System—brochure—1989.
Diacor Portalcast Block Cutting and Casting System—Preinstallation Planning Guide—1989.
Kermath Radiation Oncology Simulation Equipment brochure (T.O.P. 2000).
Kermath Radiographic/Fluoroscopic Simulator Installation Guide, Jun. 1988, "NEWS TRENDS—PC Workstation Converts CT Scan Images into 3D"—Machine Design Magazine, Nov. 24, 1988—p. 20.

Primary Examiner—Edward P. Westin
Assistant Examiner—Kim-Kwok Chu
Attorney, Agent, or Firm—Griffin Branigan & Butler

[57] ABSTRACT

A simulation/generation/verification system for blocker patterns and blockers for use in radiation therapy comprises a fluoroscopic simulator apparatus, a computer system for acquisition and processing of fluoroscopic images, a manual input device for superposing blocker pattern outlines onto such images, display and storage devices for such images, apparatus for automatic cutting of blocker contour templates, blocker patterns and blockers, and apparatus for verification thereof. The system also facilitates acquisition of compensator contours and generation of corresponding compensator filters for incorporation with blockers. The system facilitates simulation, generation, and verification of blocker patterns or blockers per se in one substantially continuous procedure that minimizes intervening manual steps, while a patient is aligned within the system during an uninterrupted session. Computer-aided and computer-controlled fluoroscope image composition, linearization, enhancement and manipulation, marking of target field, acquisition and appropriate manipulation and superposition of compensator contour information, recording of all of such information and use thereof for automatic cutting of blocker contour templates, compensator filters, blocker patterns or blockers and immediate verification thereof facilitate time and cost savings, improvement in blocker accuracy, and reduction of patient anxiety and discomfort.

45 Claims, 8 Drawing Sheets

METHOD AND APPARATUS FOR GENERATING RADIATION BLOCKERS

This invention relates to apparatus and method for simulating, generating, and verifying blockers and/or patterns therefor for use in radiation therapy and, in particular, it relates to acquisition, storage, and manipulation of fluoroscopic images by computer for generation and simulation of blocker (mask) silhouettes, to fabrication of blockers and blocker patterns and to verification thereof on a radiographic/fluoroscopic simulator.

A variety of devices are presently used in radiation therapy procedures for producing so-called blockers (masks) of radiation-impermeable or radiation attenuating alloys for radiation masking of all but specifically designated body areas. Commonly, a patient is positioned in a radiographic/fluoroscopic simulator that produces real-time fluoroscopic images, as well as being capable of providing X-rays (films). The physician positions, under fluoroscopy conditions, field-defining wires in the simulator to outline the desired target area and one or more x-ray films are exposed that show the entire field including the superposed field-defining wires. The patient is dismissed and x-ray films are developed and, thereafter, the target area is manually marked on the film to further define the designated area for irradiation. Also compensator contours are defined for generation of compensator filters.

A blocker pattern is then conventionally produced from a sheet of polystyrene foam material by manual tracing of the target area (intended blocker) silhouette or contour marked on the x-ray film. This is performed in an apparatus that cuts a polystyrene foam block in the appropriately scaled-down silhouette outline along lines (rays) originating at a point (the origin of radiation). Cutting of the foam block is conventionally done by a heated wire or by an appropriate milling machine arrangement. A compensator filter pattern may be also produced for use in conjunction with such a blocker pattern. Thusly obtained patterns are further utilized for casting of blockers (masks) and compensator filters from appropriate radiation-impermeable or radiation-attenuating alloys. A cast blocker (and a compensator filter) is eventually inserted and aligned in the radiation path of a radiation therapy apparatus, as for instance represented by cobalt sources or by linear accelerators and the like. Before treatment commences, a blocker is sometimes verified for its accuracy and alignment either in a radiographic/fluoroscopic simulator or in the actual radiotherapy apparatus (whilst the patient is aligned therein).

For instance, radiotherapy simulators are marketed in the U.S.A. by the Varian Company, Palo Alto, Calif., under the name Varian Ximatron C-series Radiotherapy Simulators, and by the Kermath Manufacturing Corporation, Richmond, VA., under the name Kermath Radiographic/Fluoroscopic Simulator. The Kermath Manufacturing Corporation also manufactures computer assisted tomographic (section scanning) apparatus, for instance a system entitled the T.O.P.2000 System, that is used in radiotherapy simulation. The Portalcast Block Casting System by Diacor, Salt Lake City, Utah, for example, markets heated wire cutting apparatus for blocker patterns and casting apparatus for casting of blockers.

Whereas present systems for the provision of blockers are in many ways not unsatisfactory, the involved procedures are relatively cumbersome, time consuming, and are subject to human error and to errors due to inaccuracies of existing equipment. For instance, the need for a special visit of a patient to a facility specifically only for initial determination of the radiation target area or field (after which the patient is dismissed), the consequent need for processing of x-ray film and marking of target outline thereon, and the need for subsequent cutting of the blocker pattern and casting of the actual blocker, before the blocker may be verified (in advance of treatment) in the course of another special visit by the patient to the facility, are all rather time consuming, costly, and not exactly tranquility-promoting for the patient. Moreover, the described procedure may need to be repeated, if the blocker turns out to be inaccurate or in error during verification. In view of the required steps and passage of time between steps (commonly amounting to at least several days), errors occur not only due to accuracy limitations of equipment and human failing, but also, for example, due to size, shape and position changes of tumors. Manual marking of target outlines on an x-ray film and subsequent manual tracing of such outlines on a blocker pattern cutting apparatus contributes to incidence of inaccuracies and errors.

In view of the foregoing, it is an object of the present invention to provide apparatus and method for simulating, generating, and verifying blocker templates, blocker patterns and/or blockers in one substantially continuous uninterrupted accurate procedure that minimizes manual intervening steps, in particular by use of computer-aided and computer-controlled fluoroscope image composition, linearization, enhancement and manipulation, marking of target field and silhouette, recording of such information and use thereof for automatic cutting of blocker templates, patterns and/or blockers directly for immediate verification on the patient and including generation and automatic fabrication of compensator filters ready for use in radiation treatment.

SUMMARY OF THE INVENTION

In accordance with principles of the present invention, a patient is appropriately positioned within a fluoroscopic apparatus and fluoroscopic images of specific body regions are digitized and acquired ("grabbed") by conventional computer equipment available for such uses. The grabbed images are processed and stored in a computer and are displayed on monitor screens. Such images include planar views as well as tomographic sections generated by the apparatus in cooperation with appropriate computer control and processing.

The attending physician/oncologist manipulates displayed images via appropriate computer input and traces the outline of the target field (for eventual irradiation) on the display screen by means of conventional computer accessories, for example a light pen or a mouse. Once a satisfactory target contour (overlayed on the image) is found, it is recorded together with the image itself. At this time, a blocker pattern cutting device that is controlled automatically by the computer cuts a blocker paragon in form of a blocker contour template or a blocker pattern (of the target contour) from a blank of an appropriate material (for instance styrofoam or other material) in accordance with the recorded overlay image. For example, a styrofoam blank is precoated or preimpregnated with barium or the pattern itself is treated with barium subsequent to cutting, so that the pattern becomes partially opaque to x-rays. Other precoating or postcoating includes impregnation or coating with aluminum or other appropriately partially opaque materials.

This template or blocker pattern is now placed in proper registration within the fluoroscopic apparatus as a mask in front of the x-ray source and it is verified in regard to registration alignment and accuracy of the cut contour in relationship to the patient (who is still positioned in the apparatus) by use of the fluorocope and x-ray facility of the apparatus. Images obtained and prior images are superposed, or compared side-by-side or otherwise manipulated in various conventional ways, and such overlay images are recorded and stored. X-ray film of the verification (overlay) images may be taken for record purposes.

Successful verification of a blocker template is consequently followed by the automatic cutting of the actual blocker pattern in conformance with substantially the same computer-cum-cutting-device set-up as had been used to cut the template. Alternately, if the step of cutting and verifying of a template is omitted, a blocker pattern per se is cut and verified. In either case, adequate verification has been performed.

A blocker pattern that has been verified (by itself or by its template) is now ready to be used in a conventional blocker casting process that provides an actual blocker from radiation-impermeable or radiation-attenuating alloy within less than one half hour. Thereafter, the blocker is inserted in appropriate position in a radiation therapy apparatus to shield all but those patient body areas required to be irradiated. The blocker may include a compensator filter for detailed relative radiation dosage compensation (attenuation) in different regions of the target area.

As hereinbefore indicated, a blocker pattern is produced by cutting of a styrofoam blank. This cutting operation may be performed in a conventional heated-wire cutting device or a special milling cutter device, but whose cutting operation is automatically controlled, according to principles of the present invention, by a computer in accordance with the stored overlay images. In another embodiment in accordance with the principles of the invention, the blocker pattern is produced in a laser cutting apparatus that is similarly automatically controlled and that operates with significantly improved efficacy, accuracy, speed, and other like advantages. Moreover, the automatically controlled laser cutting apparatus may be used to directly cut appropriate alloy blockers per se, thusly further simplifying the procedure and improving speed, accuracy, and reducing cost and incidence of errors.

In a further embodiment of this invention, blocker templates and patterns and blockers per se, i.e. blocker paragons, as well as patterns or molds for compensator filters and compensator filters per se, are automatically fabricated in a numerically controlled multi-axis milling apparatus under computer control and supervision in accordance with appropriate contours stored in the computer.

According to yet another embodiment of the present invention, computer-stored images of blocker contours are used to preselectably and automatically adjust blocker aperture size and shape in certain existing radiation treatment equipment that has presently only facilities for manual adjustment of aperture size and shape in form of a plurality of individually selectively adjustable blocker leaves. Automatic selective adjustment of individually motorized leaves is performed under computer control and supervision.

In comparison with existing equipment and conventionally applied procedures, apparatus and method of the present invention provides for very significant time and cost saving, improved accuracy of irradiation, and substantial reduction of patient anxiety and discomfort, as well as a reduction in patient exposure to x-rays during simulation and verification due to use of fluoroscopy (reducing the number of x-ray film exposures conventionally needed during such procedures). Whereas presently a patient needs to visit a facility especially for the simulation procedure and has to return some days later for verification of a blocker, before radiation treatment may commence (and this procedure may have to be repeated), the present invention facilitates a combination of simulation and blocker or blocker pattern verification in a single short visit.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference numerals refer to like parts throughout different views. The drawings are schematic and not necessarily to scale, emphasis instead being placed upon illustrating principles of the invention.

DESCRIPTION OF THE PREFERRED EMBODIMENTS

Figure 1:
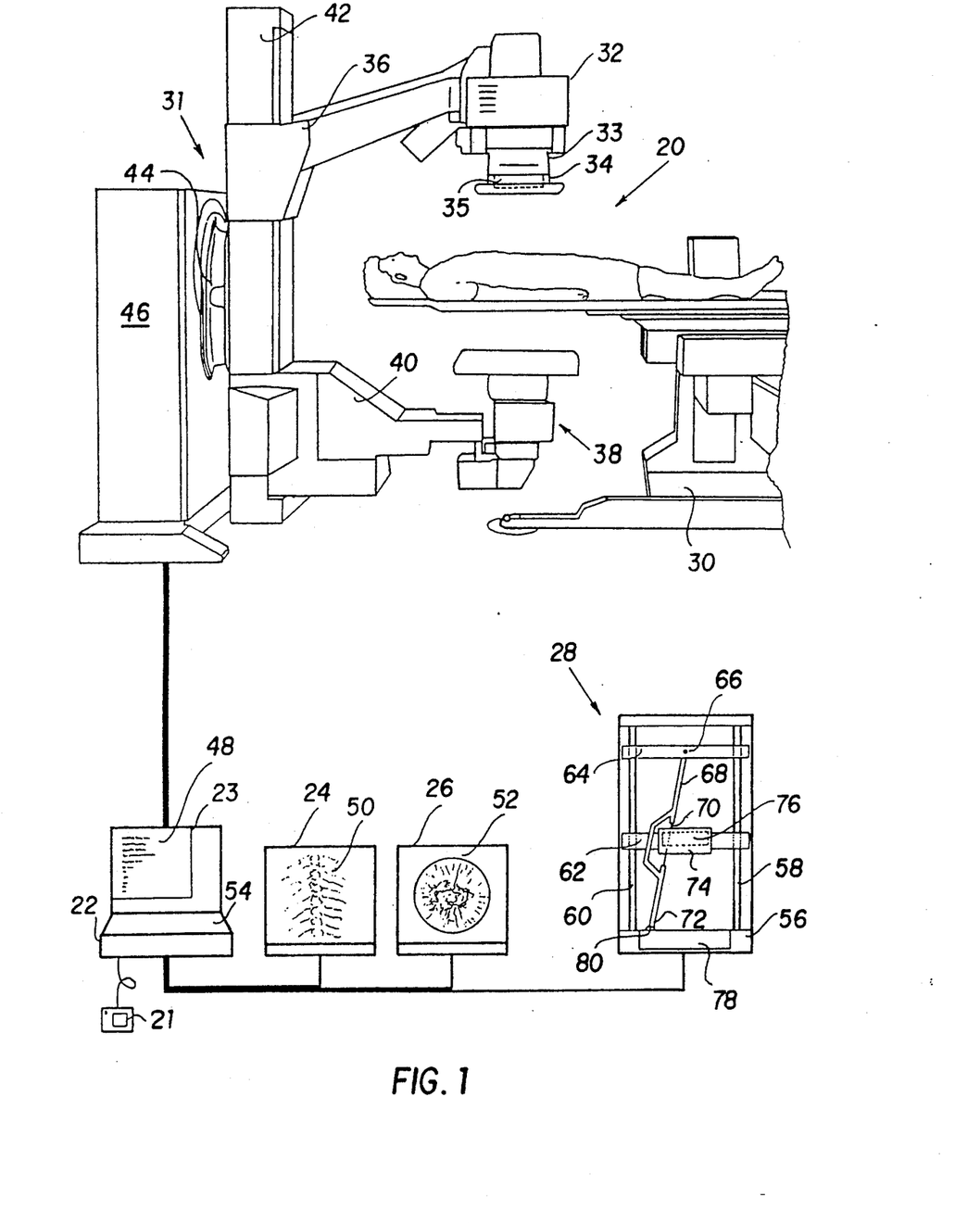
FIG. 1 is a schematic composite frontal view of a simulation/generation/verification system for radiation therapy blocker patterns and/or blockers according to principles of this invention.

Referring now to FIG. 1 of the drawings, numeral 20 designates a fluoroscopic simulator shown in the upper half of the drawing. A computer 22, having a computer display 23, is shown connected to simulator 20 via an electrical cable. A first and a second monitor 24 and 26 are connected to computer 22 for displaying of images and a mouse 21 (alternately a light-pen or similar arrangement) is connected to computer 20 for image manipulation, control, generation of image-superposition contours, and for other control functions. Computer 20 is further connected to a cutting device 28.

Simulator 20 comprises a table arrangement 30 to support and align a patient in appropriate position for fluoroscopy and tomographic scanning and a fluoroscope device 31 therefor. Fluoroscope device 31 comprises an x-ray head 32 that is disposed in adjustable cantilevered manner on a carriage 36, an image intensifier head 38 disposed in adjustable cantilevered manner on a support 40, and a track pillar 42 along which carriage 36 and support 40 are independently adjustably carried. Image intensifier head 38 commonly also incorporates x-ray film holder and exposure arrangements. Track pillar 42 mounts via a rotary drive mount 44 on a support base 46 and may be adjusted to any position or rotated about a patient (for tomographic purposes). X-ray head 32 includes a horn 33 that incorporates a field mask section 34 for holding of various field defining devices and that also includes a blocker tray holder 35.

Computer 22 includes also a keyboard 54 and a display 23 with a terminal screen 48. Computer 22 further comprises conventional components, including recording and storage devices, output devices such as printers and plotters and the like. Although terminal screen 48 and monitors 24 and 26 can be used interchangeably, in general, screen 48 is used to display text, monitor 24 is used to display fluoroscopic images and composites thereof, and monitor 26 is used to display tomographic section images. Further monitors may be present to display additional information or images.

Cutting device 28 shown in FIG. 1 comprises a blocker pattern cutter of a conventional kind for such purposes and that is modified according to principles of this invention to facilitate automatic contour cutting under control of computer 22. Basically, cutting device 28 comprises a housing having disposed therein a cutter base 56, a pattern carriage 62, and a pivot carriage 64. Carriages 62 and 64 are adjustably mounted upon first and second rails 58 and 60. Pivot carriage 64 comprises a pivot 66 (of a ball-joint kind) to which a cutter bar 68 is attached such that cutter bar 68 is free to pivot at pivot 66. A guide end 72 is provided at the lower end of cutter bar 68. Along its length, cutter bar 68 has a bow-like section to by-pass pattern carriage 62 and a shunt portion including a heated wire 70 for cutting styrofoam blanks. Pattern carriage 62 comprises a pattern mount 74 that serves for holding of styrofoam material whilst it is being cut by heated wire 70. The styrofoam material or the resulting pattern is indicated schematically by outline of a blocker pattern blank 76.

Cutter base 56 is provided with a motorized two-axis positioner 78 that engages guide end 72 of cutter bar 68. For this purpose, a ball-joint connector 80 is disposed on positioner 78 such that guide end 72 is securely guided along both horizontal axes (by positioner 78) while cutter bar 68 is moved about pivot 66 angularly. Cutter bar guide end 72 telescopes within ball-joint connector during such motion or cutter bar 68 itself telescopes.

Conventionally, unmodified manually operated cutting devices are provided with a light within cutter base 56 (in place of two-axis positioner 78) upon which x-ray film is placed and desired blocker contours are manually traced by moving guide end 72 by hand. In accordance with principles of the present invention, the operation of motorized two-axis positioner 78 is connected to and controlled directly by computer 22. Motorized two-axis positioner 78 is of a commercially available type as will be further described hereinafter.

Figure 2:
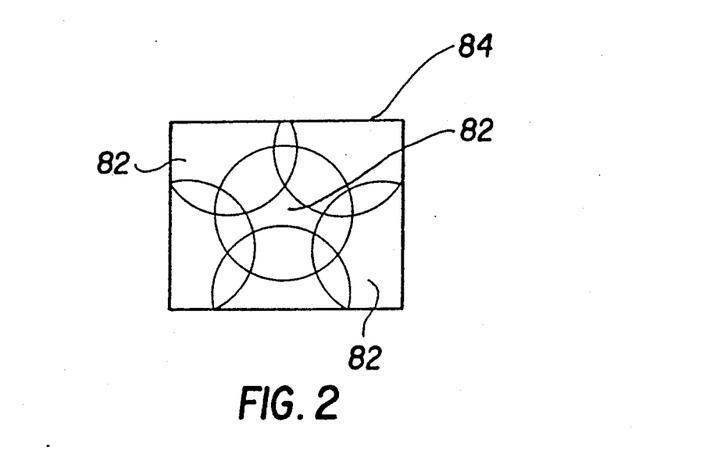
FIG. 2 is a schematic depiction of a composite display image according to principles of this invention.

FIG. 2 indicates schematically the manner in which a plurality of individual fluoroscopic images 82 acquired from the image intensifier (comprised in image intensifier head 38 shown in FIG. 1) is composed to arrive at a computer-generated composite image 84. An image available from the fluoroscope image intensifier is generally of a smaller size than the field covered by an x-ray film. For instance, the actual useful image size from the image intensifier is conventionally 10.7 inches in diameter, while the corresponding x-ray film image taken on the same equipment and having the same magnification provides a format and size of 14 by 17 inches. Whereas the smaller fluoroscopic image has been used for general viewing, a physician requires the larger image (x-ray size) to determine exact treatment contours. Moreover, conventional intensifier images suffer from distortions, such as those due to fluoroscope curvature and others caused by the intensifier device. Consequently, determination of blocker contours and other radiation parameters has been based on the more accurate x-ray film that covers a larger field.

According to principles of the present invention, fluoroscope images representing overlapping offset fields are acquired (grabbed) by computer 22, are linearized and corrected for curvature and other fluoroscope distortions, and are computer-enhanced and composed into a composite image 84 of the size, format, and coverage of a conventional x-ray film (as indicated in FIG. 2). Composite image 84 is provided (by appropriate programming of computer 22), for alignment purposes, with optionally selectable operator-movable rectilinear target field delineating lines and with stationary cross-hairs defining the center of the x-ray field (and of the treatment equipment radiation field). Additionally, composite image 84 is provided with computer-generated reticles for linear measurement and scaling purposes. Such facilities are provided in conformance with conventional equipment facilities, wherein four independently movable motorized wires are commonly provided for field delineating purposes, wherein fixed-position cross-wires are employed for centering, and wherein metal beads of fixed size in specific locations are commonly used for establishment and confirmation of image scaling. Conventional equipment provides (at high cost) these mechanical facilities which are disposed in the x-ray head for projection upon fluoroscope and x-ray film (as well as for light-field projection). However, aside from the relatively high cost of these facilities, projection results in undesirable comparatively large obstructions of images due to the inherent magnification. For instance, field-delineating wires of smallest practical diameters still project upon x-ray film or fluoroscope as approximately pencil-thick lines. The computer-generated "projections" in accordance with the present invention provide high-contrast fine line patterns at a fraction of the cost of the conventional facilities.

Figure 3:
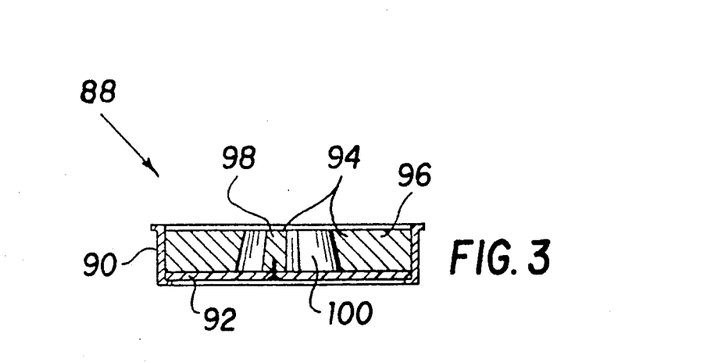
FIG. 3 is a schematic sectional view of a blocker holding arrangement that is shown for clarification purposes and that is substantially representative of existing art.
Figure 4:
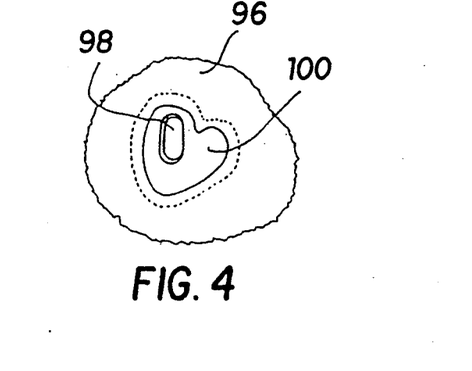
FIG. 4 is a schematic fragmental partial top view of the depiction shown in FIG. 3.

Referring now to FIGS. 3 and 4, a typical conventional blocker (or blocker pattern) holding arrangement 88 includes a blocker tray 90 within which a tray plate 92 in form of a plastic plate (generally of acrylic plastic) is securely supported and a blocker 94 that is disposed upon tray plate 92. Blocker 94 comprises at least a blocker body 96, but may comprise also one or more islands as indicated by a blocker isle 98 that is disposed within a contoured unobstructed region 100 and that is shown fastened in position on tray plate 92 by a screw or a pin, but that may be secured in proper position onto plate 92 in other conventional ways. Blocker holding arrangement 88 may also be of different structure, for instance, to suit different equipment makes. FIGS. 3 and 4 are presented here to facilitate understanding. Blocker holding arrangement 88 including blocker tray 90 may serve not only to hold an actual blocker 94, but it may serve to hold a blocker template or a blocker pattern during verification thereof in accordance with the present invention. It should be understood that a blocker pattern is an inverse or negative of a blocker in order to serve as a mold for casting of such a blocker. Blocker patterns are generally of polystyrene foam material and actual blockers are conventionally fabricated by casting (using blocker patterns as molds) from low melting temperature and high density alloys that are radiation impermeable or radiation attenuating.

Blocker holding arrangement 88 is suited to insertion into blocker tray holder 35 in x-ray head 32 (shown in FIG. 1) for verification of a blocker paragon, i.e. blocker 94 or a blocker template or a blocker pattern, and also for insertion into appropriate location in a radiation treatment machine for verification purposes and for the actual irradiation process (in the latter case only a final blocker is applicable).

Unobstructed region 100 is provided with tapering sidewalls at angles that are the same as angles of rays tangent thereto and originating at the point of origin of the radiation source of the fluoroscopic apparatus and the radiation treatment machine when blocker 94 (or a blocker pattern) is appropriately positioned in such equipment.

Blocker patterns are conventionally fabricated or cut for the purpose of providing patterns and cores for molds for casting of the actual alloy blockers, as hereinbefore indicated. Such conventional blocker patterns are not verified before casting of alloy blockers. Cast alloy blockers are sometimes verified in simulators, or more commonly in actual radiation treatment equipment by exposure of x-ray film through a blocker inserted into the equipment and by manual overlay over the original film that is marked up with a blocker contour. Sometimes such a verification (so-called "port verification") includes also further x-rays of the patient with and without interposition of the alloy blocker. In any case, if only finished blockers are verified, the costly and cumbersome procedure that precedes this lacks precision and, if a blocker is rejected, the entire blocker-generating process has to be repeated. If blockers are not verified, significant danger and risk is involved in radiation treatment error due to the not insignificant incidence of misaligned or misshapen blockers.

The present invention facilitates immediate generation, fabrication, and verification of a blocker pattern while the patient is still aligned within fluoroscopic simulator 20. According to principles of this invention, styrofoam blocker patterns are treated so that they become slightly opaque to x-rays such that they may be verified fluoroscopically without blocking the image entirely. This is achieved by precoating or preimpregnating of the blocker pattern blank either on its upper or on its lower surface (or on both surfaces) with barium or appropriate barium salt solution (or with other suitably partially radiation opaque materials). Alternately, such coating or impregnating is performed subsequent to cutting of the pattern.

The present invention also facilitates immediate generation, fabrication, and verification of a blocker template that is a substantially two-dimensional version of a blocker pattern and that facilitates verification of a computer-processed and stored blocker contour. Time is saved in cutting of such a template and in its handling during verification on the fluoroscopic apparatus particularly because the template comprises only a single piece of sheet material of relatively small thickness, whereas fabrication and preparation of a blocker pattern for verification purposes generally involves handling and alignment of more than one pattern component with a thickness of several inches. Blocker template fabrication and verification will be described hereinafter in further detail.

Figure 5:
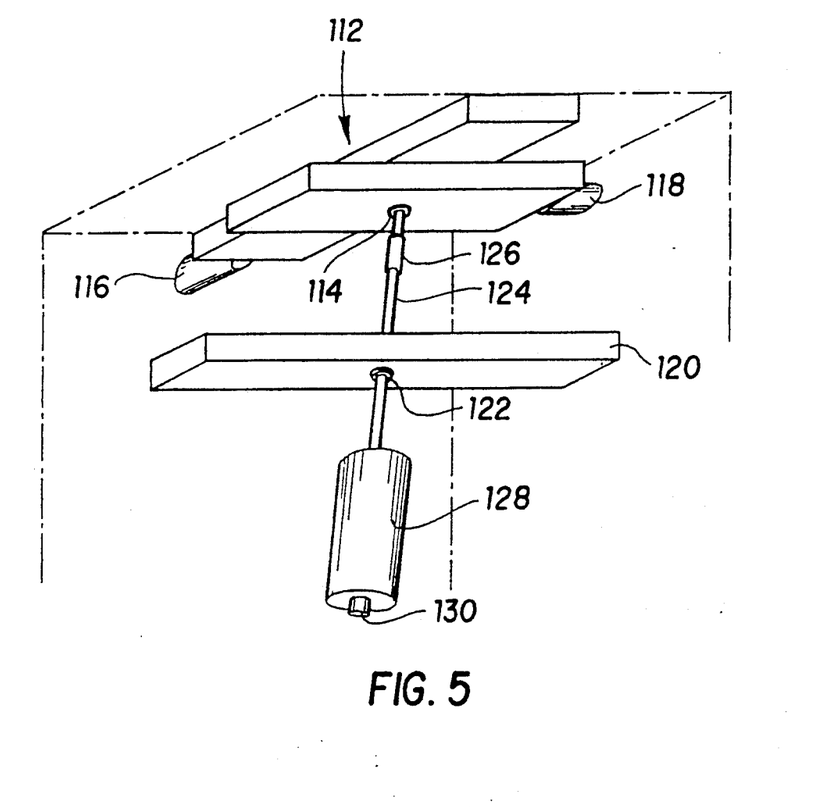
FIG. 5 is a schematic fragmented isometric depiction of a two-axis positioning device to control blocker pattern cutting in accordance with this invention.
Figure 6:
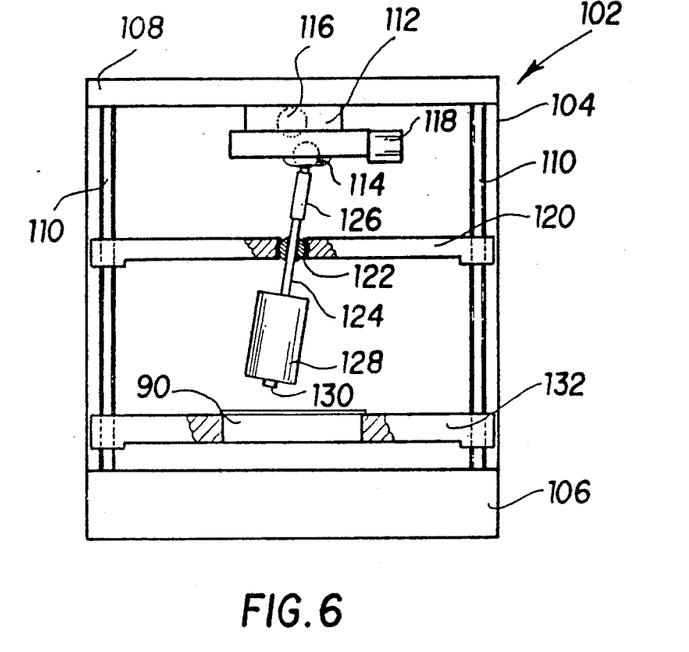
FIG. 6 is a schematic partial front elevational view of a laser cutting apparatus for blockers or blocker patterns according to principles of this invention.

Cutting device 28 (shown in FIG. 1), described hereinbefore, is replaced in a further improvement according to principles of the present invention by a laser cutter 102 shown in FIG. 6. The isometric depiction in FIG. 5 provides clarification for a portion of the mechanism. A housing 104 comprises a base 106 and an upper frame 108. Vertical rails 110 are disposed near inner sides of housing 104 and are rigidly mounted on upper frame 108 at one end and on base 106 at the other end. A two-axis motorized positioner 112 is mounted on the lower inner side of upper frame 108, approximately in the center thereof. The lowermost face of positioner 102 is equipped with a ball-joint suspension 114 secured thereto. Each slide of positioner 102 is provided with a motor, namely upper slide motor 116 and lower slide motor 118, each of which is electrically connected to and controlled by computer 22. Two-axis motorized positioner 112 is of a conventional kind, for instance as commercially available from Automation Gages Inc., Rochester, N.Y., as Series X-Y Motorized Positioning Stage. Stepping motors are used to drive the stages, although other conventional drives, such as positioning servos, may be employed.

A horizontally disposed pivot bar 120 is carried by rails 110 to facilitate vertical repositioning, adjustment, and secure locking at any height. A ball-joint pivot 122 is disposed approximately in the middle of pivot bar 120. A guide rod arrangement 124 that includes a coupler 126 is suspended from ball joint suspension 114 (in freely pendulous manner) and is guided through and in ball-joint pivot 122 so that guide rod arrangement 124 is restrained from lateral movement and is only permitted motion along its axis through and angular motion about pivot 122. Rigidly affixed to the lower end of guide rod arrangement 124 is a laser 128 whose optical axis is oriented in line with guide rod arrangement 124 and therewith in line with ball-joint pivot 122 and the pivot center of ball-joint suspension 114. Laser 128 is of a kind conventionally utilized for material cutting operation and produces a correspondingly narrow high-intensity beam centered about its optical axis. The beam exits laser 128 through the center of aperture 130.

A horizontally oriented tray carriage 132 is disposed below pivot bar 120 and is carried by rails 110 to facilitate vertical repositioning, adjustment, and secure locking at any height (that clears laser 128). Tray carriage 132 carries and securely holds blocker tray 90 (shown in more detail in FIG. 3). Blocker tray 90 may hold an appropriate blocker pattern blank (as hereinbefore described) or an appropriate alloy blank for cutting of an actual blocker by laser cutter 102. In this respect only with regard to the shape of cut blockers or blocker patterns, the description of shape of blocker 94 given in conjunction with FIGS. 3 and 4 is referred to hereby.

The vertical distance between a blocker and a blocker pattern (carried in tray 90) and the pivot point of ball-joint pivot 122 is adjusted in laser cutter 102 for the cutting operation to be exactly the distance between a blocker or pattern in x-ray head 32 and the x-ray source point (origin) in fluoroscopic simulator 20 to achieve compatibility of size and side-wall slopes. The same distance is used in actual radiation treatment equipment (referred to the radiation source point). Similarly, pivot 122 (or analogously x-ray source point or origin of radiation) and the center of a blocker or a pattern carried in tray 90 are vertically aligned. As a matter of course, this distance (and alignment) is generally standardized among such equipment including simulators and actual radiation treatment devices.

Further, the pivot point of ball-joint suspension 114 is in vertical alignment with ball-joint pivot 122 as a reference for computer-controlled two-axis motions of motorized positioner 112. The vertical distance between the pivot point of ball-joint suspension 114 and ball-joint pivot 122 is not necessarily fixed, but, whatever distance is chosen, appropriate commensurate scaling is applied in the computer control for positioner 112. Longer vertical distances are naturally more advantageous to obtain best laser cutting accuracy. However, travel limits of positioner 112 also limit the maximum usable vertical distance.

In use of the system according to the present invention, a patient is appropriately positioned upon table arrangement 30 (FIG. 1) within the field of fluoroscopic simulator 20 and computerized tomographic section images and a plurality of overlapping fluoroscopic planar images are obtained in conventional manner. The images are grabbed by computer 22 and are processed and stored. Processing of fluoroscopic images includes image linearization and correction for fluoroscope curvature and other distortions, computer-enhancement of images and composition of overlapping images into a composite image of the size, format, and scale or coverage of a conventional x-ray film.

The resulting images are stored and displayed under computer control and according to operator demand. In general, computer display 23 serves to display text for control and supervision purposes, first monitor screen 50 displays composite fluoroscope images, and second monitor screen 52 displays tomographic section images. In view of the displayed images, the attending physician uses mouse 21 (or another convention input device, for instance a light pen) to manipulate and select appropriate images. For example, he may zoom in and out to obtain greater detail or more of an overview, or he may enlarge only particular areas located anywhere within the stored image fields, etc. The physician then traces onto the chosen fluoroscopic computer image a desired target (or blocker) contour, using mouse 21 (or a light pen or other similar input device). Once the contour is satisfactory, it is stored in appropriate registration with the corresponding image.

It will be understood that the attending physician need not be in the same room with the patient and the simulator equipment, when utilizing the system and applying the procedure in accordance with the present invention. Since the physician manipulates images and defines blocker contour entirely via computer images and computer controls, appropriate networked computer workstations may be located anywhere. Similarly, fabrication equipment could be located in any even remote locations.

Under computer control, a blocker pattern is now cut in polystyrene foam in cutting device 28 in conventional manner, except that cutting device 28 is not manually operated and controlled by manually tracing over manually marked contours on an x-ray film, but it is automatically controlled by computer 22 that commands the motions of the two-axis positioner 78 in accordance with the desired contour that has been recorded in computer memory.

In a further embodiment according to principles of the present invention, cutting device 28 of FIG. 1 is replaced by laser cutter 102, shown in FIG. 6 (and partially also in FIG. 5). Laser cutter 102 cuts, under computer control, blocker patterns not only in styrofoam, but in a great variety of other materials also. Moreover, and more importantly, laser cutter 102 cuts, under computer control, actual alloy blockers directly. In the latter case, an actual alloy blocker is fabricated and verified while the patient is still aligned in fluoroscopic simulator 20 within a few minutes of the physician having contoured the appropriate blocker silhouette on computer 22, as hereinbefore described. Direct blocker cutting eliminates the steps of pattern cutting and of subsequent blocker casting, and it avoids incidence of errors and inaccuracies during these steps. Moreover, the facilitated immediate verification allows immediate commencement of radiation treatment with insignificant delay even if a replacement blocker may have to be produced, as the entire process is accomplished within a few minutes.

In cases when blocker patterns are required, blocker pattern cutting by laser cutter 102 eliminates the conventionally required steps of drilling an initial hole through the pattern blank, feeding the cutting wire (heated wire 70) through the drilled hole, and fastening the wire to cutter bar 68.

As verification of alloy blockers is subject to inaccuracies particularly since verification images are entirely opaqued (by the alloy) in the blocked areas, blocker patterns of only partially or slightly radiation-opaque materials may be required in situations demanding particular precision of verification. Laser cutter 102 is capable of cutting blocker patterns in a great variety of appropriate materials, including for example light metals, ceramics, plastics, etc. Consequently, under such high precision conditions, an appropriate blocker pattern is cut for verification purposes only. As little cost and time is involved for laser cutting, the corresponding alloy blocker may be cut in one machine set-up immediately thereafter. A successful verification of the blocker pattern facilitates immediate subsequent commencement of radiation therapy using the actual lead blocker already cut.

In accordance with another embodiment of the present invention, computer-stored images of blocker contour overlays, as hereinbefore described for use in computer-controlled automatic blocker or blocker pattern cutting, are used to preselectably and automatically adjust blocker aperture size and shape in certain existing radiation treatment equipment having presently only facilities for manual adjustment of aperture size and shape. As shown in FIG. 11 existing manual adjustment in such known equipment relies on a plurality of radiation blocking leaves 301 appropriately disposed to allow independent adjustment of each leaf 301 into the radiation path to achieve appropriate contouring of blocker (or porting) aperture 305. For instance, the Mitsubishi International Corporation, Philadelphia, Pa., markets a line of medical linear accelerators for radiation treatment that include a so-called "22-leaf conformation collimator" as well as an asymetric collimator. Essentially, each leaf 301 of radiation impermeable material is independently adjustable into the radiation path to obtain an aperture adapted in shape and size to a particular required target field. According to the present invention, each leaf 301 is positioned by a motorized drive 308, for example a stepping motor 312, under automatic preprogrammed control of computer 22 (FIG. 1) in dependence on and in accordance with the blocker or target contour entered into the computer by the physician in operation of the fluoroscopic simulator 20 (FIG. 1), as hereinbefore described.

Figure 7:
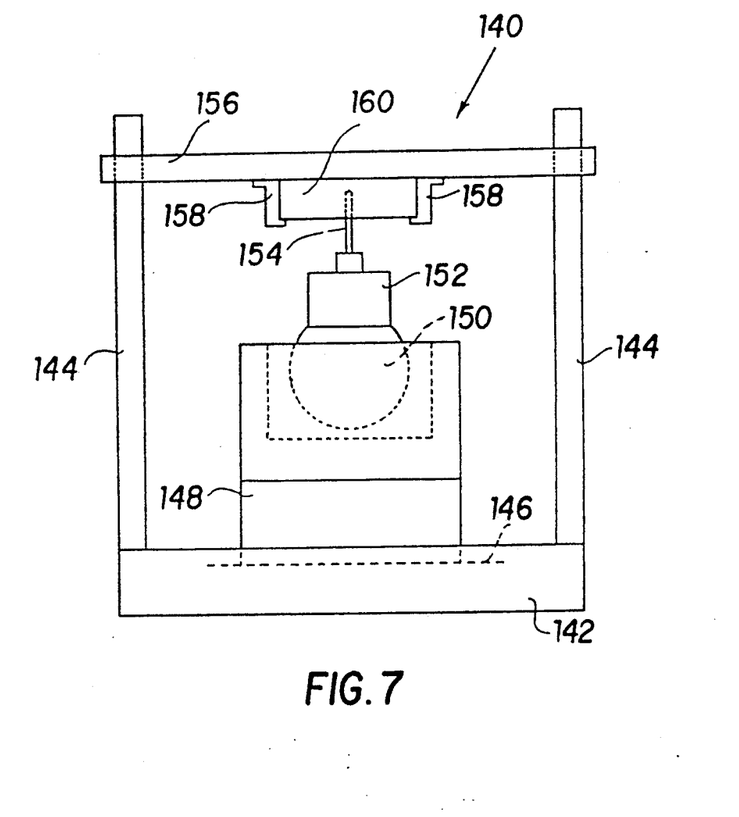
FIG. 7 is a schematic elevational view of a milling apparatus for cutting of blocker templates, blocker patterns, and blockers per se, as well as for cutting of patterns for compensator filters and compensator filters per se in accordance with this invention.

In accordance with a further embodiment of the present invention, cutting device 28 (shown in FIG. 1) is replaced by a milling apparatus 140 that is schematically depicted in FIG. 7. Milling apparatus 140 is essentially a conventional numerically computer-controlled end-milling arrangement, whose milling cutter is controllable with 5 degrees of freedom, namely along three translational axes and about two orthogonal axes of rotation. As shown, the arrangement is oriented upside down in comparison with conventional machines of this kind. In other words, the milling head is disposed above and upon the carriages to provide the appropriate controlled motions, while the workpiece is disposed above the milling head. Milling into the workpiece is performed from below in a generally upward direction under control and supervision of computer 22 (FIG. 1).

Milling apparatus 140 comprises a base structure 142 and a frame structure 144 mounted thereupon. Base structure 142 includes a horizontal first axis carriage upon which an orthogonally movable horizontal second axis carriage 148 is translatably disposed. A gimbals arrangement 150 is mounted on second axis carriage 148 to provide rotation about two horizontal orthogonal axes for a milling head 152. A milling cutter 154 (generally a ball-endmill cutter) is driveably mounted within milling head 152. Frame structure 144 supports a horizontal work platform 156 in vertically adjustable manner. One or more work holders 158 are fastened onto the lower face of work platform 156 for secure holding of a workpiece 160 in an accurately registered location. Workpiece 160 is easily mountable in and dismountable from its registered location. For this purpose, work platform 156 is adjustably movable vertically upward along frame structure 144. A vertical axis translational slide carriage is incorporated either in base 142 or in the adjustable support arrangement of horizontal work platform 156 on frame structure 144. Alternately, milling head 152 incorporates a slide carriage arrangement to provide feed motion for milling cutter 154 (along its axis).

Carriages 146 and 148 (along their axes), gimbals arrangement 150 (about its two axes), and the vertical axis translational slide carriage or the slide carriage arrangement incorporated in milling head 152 are motor driven under numerical control in conventional manner. Control and supervision is provided therefor by computer 22 (FIG. 1). Milling apparatus 140 serves for milling of blocker templates, blocker and compensator filter patterns, and it may be used to cut blockers and compensator filters directly. Moreover, milling apparatus 140 mills blocker/compensator combinations or patterns therefor, as will be hereinafter described.

Figure 8:
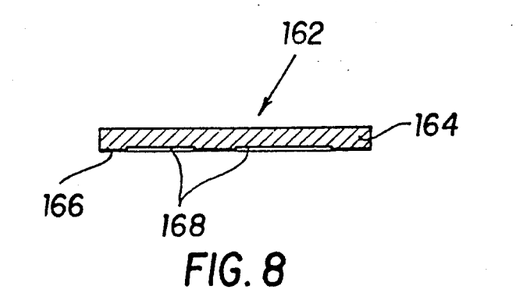
FIG. 8 is a schematic sectional view of a blocker template in accordance with the present invention.
Figure 8A:
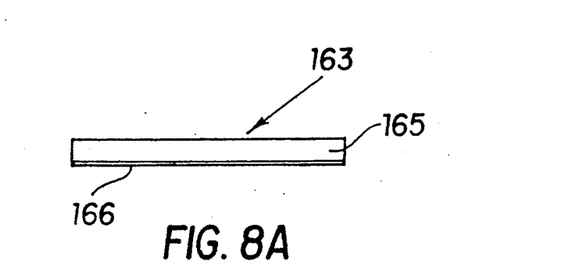
FIG. 8A is a schematic side view of a blank for the blocker template depicted in FIG. 8.

Referring now to FIGS. 8 and 8A, a blocker template 162 is shown after it has been milled in milling apparatus 140 from a relatively thin sheet template blank 163. Template blank 163 comprises a blank body 165 and a surface layer 166. Blocker templates serve for verification purposes of blocker contours (traced by the physician/oncologist for irradiation) retained by the computer and of the computer-controlled blocker fabrication procedure. Various materials that are substantially transparent to x-rays are suitable as blank body 165 of template blank 163. Styrofoam represents one of a number of suitable materials for this purpose, particularly since it is a material that is conventionally also used for blocker patterns and has proven itself to be easily machinable and is accepted in the art of blocker pattern fabrication. Other suitable materials for template blank bodies 165 include Plexiglas, Lexan, and similar visually transparent plastics for reason of their transparency, as will be discussed hereinafter. Blank body 165 for blocker templates 162 is further provided with a partially radiation-opaque surface layer 166 that is milled away in layer removal regions 168 (for instance, corresponding to silhouettes of unobstructed regions 100 in FIGS. 3 and 4). Layer removal regions 168 correspond to those radiation target regions (or blocker contours) which have been traced by the physician onto the fluoroscopic computer images during the simulation procedure, as hereinbefore described.

Surface layer 166 is provided in form of a coating or surface impregnation of blank body 165 with a partially radiation-opaque material. For example, coating with a barium or similar salt solution or with metal powders (in appropriate binders) is appropriate for styrofoam blanks. Solid plastic (visually transparent) blank bodies may be similarly treated. Another preferred blank body material is Plexiglas or Lexan mirror material, wherein generally a thin layer of aluminum (and a protective coating thereover) covers one face of the sheet. Another preferred blank material is a plastic sheet that is coated with a strippable surface film similar to "cut-and-strip" films used in graphic arts, for instance under the trade name "Rubylith". However, for purposes of the present invention, the surface film contains metal powders that are partially opaque to x-rays rather than being opaque only to a portion of the visible light spectrum as is the case for the indicated Rubylith material.

Such a surface film (surface layer 166) need not necessarily be milled away, but it may be cut along the predefined contour lines, for example by a knife blade, a sharp point, a point graver, or by a revolving point engraving bit, as conventionally practised, whereby the particular tool is used in place of milling cutter 154 in milling apparatus 150. Appropriately computer-controlled, milling apparatus 150 cuts thusly the required template contour through surface layer 166. The surface film (surface layer 166) in the respective layer removal regions 168 is, thereafter, stripped or peeled off between contour cut lines.

It will be understood that blocker template 162, whether fabricated from coated styrofoam or coated solid plastic, will be transparent to x-rays in the layer removal regions 168, whilst it remains partially opaque in the regions where surface layer 166 has been retained. Since the blocker template 162 is machined under computer control, for example in milling appartus 140, in accordance with the blocker contours traced by the physician, as hereinbefore discussed, template 162 is used to verify such contours and the correctness of the programmed machining procedure. A machined blocker template 162 is appropriately inserted into fluoroscopic simulator 20 in proper registration, for instance in blocker tray holder 35, and fluoroscopic images as well as x-ray films serve to verify the template's contours. Additionally, if blocker template 162 is fabricated from a blank body material that is visually transparent, its contour shape and alignment relative to the patient's body surface may also be verified by collimated light being projected therethrough upon the patient's body. A collimated light source in x-ray head 32 is conventionally available for purposes of alignment of a patient in fluoroscopic simulator 20. Similarly, such a facility is available in irradiation equipment, wherein it may be utilized to similarly verify blocker contour and patient alignment by use of a blocker template 162.

Conventionally, final alloy blockers per se are used for patient alignment purposes by means of through-projection with collimated light. Since final alloy blockers are not partially transparent to x-rays, conventionally commonly performed verification on irradiation equipment by exposure of x-ray films through the blocker produces images through unobstructed blocker regions only. Consequently, the field surrounding such regions is unavailable for a reference and accurate blocker verification is difficult and suffers from significant inaccuracies. As opposed to this, the use of a blocker template according to the present invention, for such verification in irradiation equipment instead of or in addition to the use of a final alloy blocker per se, provides a full size x-ray field image that is only slightly darkened or shadowed over the blocked areas just adequately to clearly outline the blocker contour. Verification of shape and alignment is thusly much less difficult and less subject to inaccuracies.

In reference to the provision of compensator filters for use in conjunction with blockers for radiation treatment purposes, the following brief clarification may promote better understanding. Essentially, blockers are provided in the radiation path to serve as masks that permit radiation to reach only predefined body areas. Compensator filters intercept the radiation that passes through unobstructed regions of blockers and selectively attenuate such radiation to different degrees in different locations in order to avoid unnecessarily excessive radiation dosages due to relative tissue thickness and density variations. Additionally, compensator filters are adjusted in their local attenuation to provide different radiation dosages in different localities in accordance with predefined dosimetry maps to achieve the intended irradiation and thusly treatment effect. Consequently, whereas blockers could be considered essentially as two-dimensional masks, compensator filters are inherently three-dimensional structures that impose different attenuation in different locations.

For example, acquisition of information for compensation for tissue thickness may be provided by conventional equipment, such as is, for instance, available from the Huestis Machine Corporation, Bristol, R.I., under the name "Compuformer". Tissue density information may be also acquired by the computer system by quantification of local density values of x-ray film, of fluoroscopic images, and tomographic section images in relationship to corresponding location coordinate information. Adjustment of compensator filter contours in accordance with dosimetry information further modifies such information to establish compensator filter contours. All such information is acquired by the computer system and is appropriately processed for numerical control of machining of a compensator filter or a pattern (mold) therefor.

Conventionally, blocker contours are defined by the oncologist subsequent to the simulation procedure performed on a fluoroscopic simulator. During the simulation procedure, the patient is appropriately positioned and aligned with the aid of fluoroscopy. Additionally, tomographic sections (based on fluoroscopic procedures) are obtained and x-ray films of pertinent views are taken. The oncologist defines the blocker contour by tracing it onto the respective x-ray film. Thereafter, based on the x-ray film and on various other information and data, the radiation treatment dosimetry department establishes treatment procedures, specific radiation dosages, and other parameters, including those defining the required compensator filters. Thus, conventionally, a patient is necessarily dismissed after the simulation procedure and may have to return for additional sessions, such as might be required for blocker verification, before actual treatment is begun.

In accordance with the present invention, performance of at least the simulation procedure and a blocker verification procedure is facilitated during a single patient visit in one session. Moreover, additional savings in time and cost of simulation, generation, and verification of blockers or patterns therefor are achieved, while the accuracy of the procedures is significantly improved.

Figure 9:
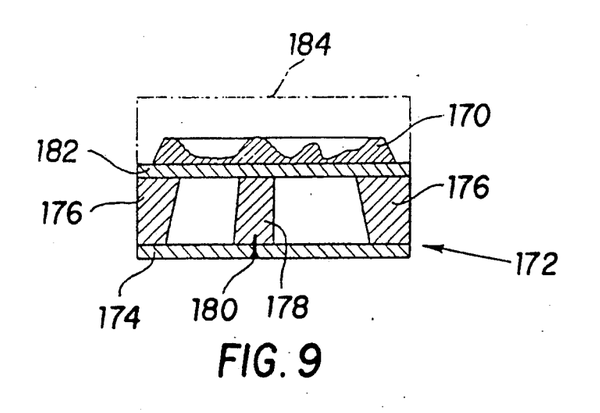
FIG. 9 is a schematic sectional view of a compensator filter stacked upon a blocker.

Referring now to FIG. 9, a compensator filter 170 is shown stacked upon a blocker assembly 172 in proper registration. Such and similarly stacked arrangements are conventionally used in radiation treatment equipment to establish the irradiated field and the local dosages. FIG. 9 is presented here in part for reference and clarification purposes. Reference is also made here to the description given hereinbefore in conjunction with FIGS. 3 and 4. Blocker assembly 172 comprises a carrier plate 174 upon which alloy blocker components are carried in registered relationship. As shown, blocker components comprise an outer blocker 176 and an inner blocker 178. The latter, being a separate component, is fastened to carrier plate 172 by fastener 180 that may comprise screws, pins, or other similar devices conventionally used for such purposes. Outer blocker 176 may also be similarly fastened to carrier plate 172 and additionally registered therewith, but it is also held in registered position thereon by inner walls of a blocker tray (not depicted here) within which the stack arrangement of filter 170 and blocker assembly 172 is carried. Carrier plate 174 is commonly a plastic plate, for instance of Plexiglas or Lexan material, that is substantially transparent to visible light, x-rays, and radiation utilized in radiation treatment equipment. Blocker components are fabricated by casting or machining from radiation impermeable materials, such as high density (low melting point) metal alloys.

An intermediate plate 182 (of similar material as carrier plate 174) is stacked upon blocker assembly 172. Compensator filter 170 is stacked on intermediate plate 182 in appropriately registered position with reference to the blocker assembly and the outline of the entire arrangement. Again, the entire arrangement and its components are appropriately fastened together in registered relationship. The arrangement is commonly held within a blocker tray (not shown here) that also serves for positioning of the arrangement within simulator and radiation treatment equipment.

Compensator filter 170 is a three-dimensionally contoured body of radiation attenuating material that is either cast in an appropriate mold or directly machined. A corresponding compensator mold 184 is outlined in FIG. 9 by phantom lines. Such a mold is fabricated from styrofoam material that is cored out by cutting with a heated wire loop or by an endmilling machine under numerical control from a computer in accordance with respective dosimetry information. In accordance with this invention, compensator mold 184 is endmilled in milling apparatus 140 (FIG. 7), described hereinbefore, or compensator filter 170 is directly endmilled in the same milling apparatus.

Figure 9A:
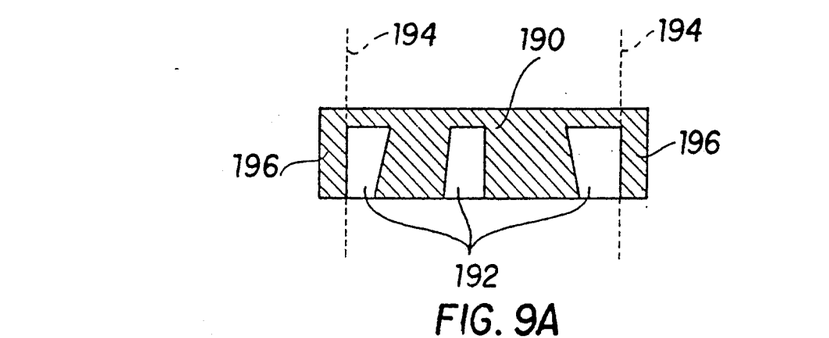
FIG. 9A is a schematic sectional view of a blocker pattern in accordance with an embodiment of this invention.

FIG. 9A depicts a blocker pattern 190 in accordance with an embodiment of the present invention for use as a mold in casting of a corresponding blocker (for example the blocker of blocker assembly 172 shown in FIG. 9). Cavities 192 are machined into the blank, for instance in milling apparatus 140 (FIG. 7), and penetrate to an appropriate depth without breaking through the entire thickness of the material. The resulting unitary structure avoids the need for aligning and holding of separate pattern parts for and during casting of a blocker. Moreover, the unitary structure of blocker pattern 190 serves to hold cast blocker components in proper relative position and alignment for mounting, for example, in blocker assembly 172 (FIG. 9). In radiation treatment use of a blocker thusly produced and mounted, blocker pattern 190 may be retained or it may be removed. The latter is easily accomplished by breaking away of the styrofoam blocker pattern material. Dashed cut lines 194 indicate where outside portions 196 are cut off, if blocker pattern 190 is retained, in order to allow insertion of a blocker assembly (for instance, blocker assembly 172 of FIG. 9), including a retained blocker pattern (for instance, blocker pattern 190 of FIG. 9A), into a blocker holding arrangement (for instance, arrangement 88 of FIG. 3).

Figure 10:
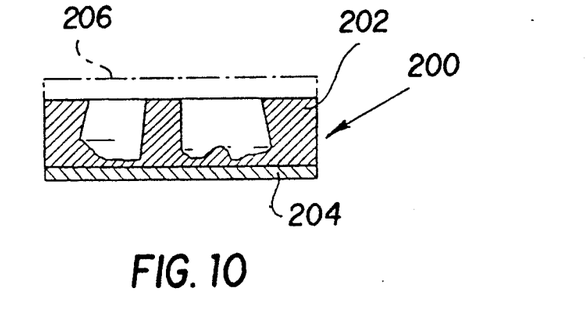
FIG. 10 is a schematic sectional view of a combined blocker and compensator filter in accordance with this invention.
Figure 10A:
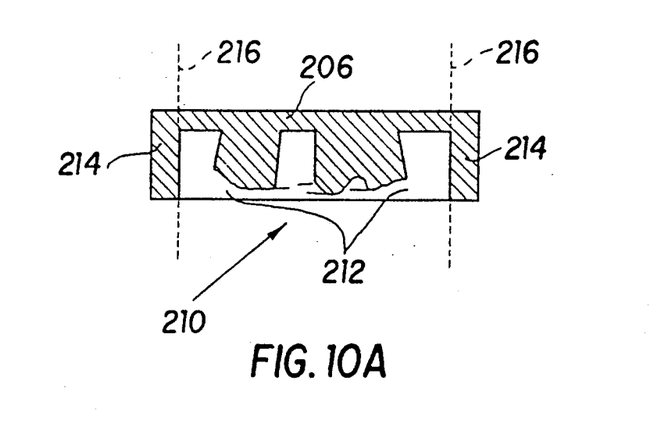
FIG. 10A is a schematic sectional view of a pattern for a combined blocker and compensator filter according to an embodiment of the present invention.

In a further embodiment in accordance with this invention, blocker and compensator filter are advantageously combined in a unitary structure. FIGS. 10 and 10A depict a blocker/compensator combination 200 and a combination pattern 210 therefore, respectively. Blocker/compensator combination 200 combines the essentially two-dimensional radiation-masking silhouette with the three-dimensionally contoured compensator filter, whereby the contours of the compensator filter are inset in the otherwise open regions of the blocker portion. This combination will be better understood in view of FIG. 9, whose separate compensator filter 170 and blocker assembly 172 are combined into the blocker/compensator combination 200 of FIG. 10 to provide the same radiation masking and attenuating effect. Blocker/compensator combination 200 comprises a combination body 202 that is carried upon a combination carrier plate 204 in registered alignment and that may be fastened together in conventional manner.

A phantom outline of a bottom mold portion 206 is shown in FIG. 10 to further indicate the manner of fabrication by casting. FIG. 10A depicts a corresponding styrofoam mold combination pattern 210 in which combination body 202 is cast. Another manner of fabrication for blocker/compensator combination 200 is by direct machining of an appropriate alloy blank under numerical computer control in milling apparatus 140 hereinbefore described in conjunction with FIG. 7.

For use of the casting process for fabrication of blocker/compensator combination 200, combination pattern 210 is milled from a styrofoam blank under appropriate numerical computer control in milling apparatus 140 (FIG. 7). A mold cavity 212 penetrates to an appropriate depth without breaking through the entire thickness of the pattern material, leaving bottom mold portion 206 intact and thusly facilitating casting when combination pattern 210 is turned upside-down from the depicted orientation. Combination pattern 210 may be removed (broken away) from the casting or it may be retained. In the latter case, outer portions 214 are cut off at cutting lines 216 (indicated by dashed lines) in order to allow insertion of blocker/compensator combination 200 (including the retained pattern portions) into an appropriate blocker holding arrangement (for instance, arrangement 88 of FIG. 3).

It will be appreciated that fabrication and use of a blocker/compensator combination offers a number of significant advantages over conventionally used separate structures for blockers and compensator filters. Advantages include higher accuracy, better alignment, faster fabrication, lower cost, etc.

It should be understood as a matter of course that accurate registration of contour images, templates, patterns or molds, and final blockers and compensator filters is provided throughout the procedures according to this invention. Computer images provide for appropriate registration marks and computer-controlled fabrication of all the indicated devices includes registration provisions such that proper alignment and registration between such devices and within simulator and radiation treatment equipment is assured.

In use of the simulation/generation/verification system for radiation therapy blockers according to the present invention, a patient is appropriately positioned upon table arrangement 30 (FIG. 1) within the field of fluoroscopic simulator 20 and computerized tomographic section images and a plurality of overlapping fluoroscopic planar images are obtained in conventional manner. The images are grabbed by computer 22 and are processed and stored. Processing of fluoroscopic images includes image linearization and correction for fluoroscope curvature and other distortions, computer-enhancement of images and composition of overlapping images into a composite image of the size, format, and scale or coverage of a conventional x-ray film.

The resulting images are stored and displayed under computer control and according to operator demand. In view of the displayed images, the attending physician/oncologist uses mouse 21 (or another conventional input device, for instance a light pen) to manipulate and select appropriate images. For example, he may zoom in and out to obtain greater detail or more of an overview, or he may enlarge only particular areas anywhere within the stored image fields, etc. The physician then traces onto the chosen fluoroscopic computer image a desired target (or blocker) contour, using mouse 21 (or a light pen or other similar input device). Once the contour is satisfactory, it is stored in appropriate registration with the corresponding image, and the numerical contour information is appropriately computer-processed for use in numerically controlled machining of blocker paragons which include blocker templates, blocker patterns or molds, and blockers per se. Moreover, three-dimensional contour information (provided to computer in conventional manner) for compensator filter patterns (molds) or filters per se, that establish relative local irradiation dosages, is also appropriately processed in readiness for numerically controlled machining.

Under computer control, a blocker template or pattern is now automatically machined and appropriately inserted into the fluoroscopic simulator 20 for verification while the patient is still positioned therein. Verification is performed, as hereinbefore indicated, and an appropriate blocker for radiation treatment is fabricated either by direct machining of a final blocker under computer control or by such machining of a pattern (mold) into which a blocker is cast. The respective compensator filter is also fabricated under computer control, again either by direct machining of the final filter or by machining of a pattern (mold) therefore into which the compensator filter is cast. As further described hereinbefore, the compensator filter may be either a separate part that is stacked with the blocker for combined use, or the compensator filter is fabricated under computer control in combination with the blocker in a unitary structure, as shown in FIG. 10A. A blocker and a compensator filter is thusly readied for use in radiation treatment equipment.

As hereinbefore indicated, a verification procedure in radiation treatment equipment may advantageously also use a blocker template that has been fabricated for verification in the fluoroscopic simulator. The template's capabilities facilitate not only light-field projection (as a blocker does), but also permit viewing of the entire field by means of exposure of x-ray film (which a blocker does not permit).

As a result of the use of the system according to the present invention, not only time and costs are saved and accuracy of blocker contours and alignment thereof is significantly improved, but patient exposure to x-rays and radiation is reduced.

While the invention has been particularly shown and described with reference to preferred embodiments thereof, it will be understood by those skilled in the art that various changes and modifications in form and details may be made therein without departing from the spirit and scope of the invention.

The embodiments of the invention in which an exclusive property or privilege is claimed are defined as follows:

1. A system for generating radiation blockers, said system including a fluoroscopic simulator for generating a fluoroscopic image of a patient and comprising:
   cutter means;
   computer means for digitized processing of said image and control of said system, said computer means including image grabbing means for grabbing and processing said fluoroscopic image to convert said fluoroscopic image to a computer-handleable image to further process said image and, to generate cutter control signals;
   means for delivering said cutter control signals to said cutter means, said cutter means being operative in response to said cutter control signals for cutting a blocker or blocker pattern corresponding to said image.

2. A system according to claim 1, wherein said cutting means is a heated-wire cutter comprising a two-axis positioner for positioning said heated wire during cutting.

3. A system according to claim 1, wherein said cutting means is a laser cutter comprising a two-axis positioner for positioning of a laser beam during cutting.

4. A system according to claim 1, including blanks for said blocker patterns, said blanks being comprised of heated-wire-cuttable material that has a radiation opaquing material applied thereto so that said blocker pattern is at least partially radiation opaque.

5. The system of claim 4 wherein said blanks are comprised of styrofoam.

6. A system for generating radiation blockers, said system including a fluoroscopic simulator for generating a fluoroscopic image of a patient and comprising:
   cutter means;
   computer means for digitized processing of said image and control of said system, said computer means including image grabbing means for grabbing and processing said fluoroscopic image to convert said fluoroscopic image to a computer-handleable image to further process said image and, to generate cutter control signals;
   means for delivering said cutter control signals to said cutter means, said cutter means being operative in response to said cutter control signals for cutting a blocker or blocker pattern corresponding to said image; and,
   wherein said blanks are comprised of styrofoam and said opaquing material includes barium.

7. The system of claim 4 wherein said opaquing material includes barium.

8. A system for generating radiation blockers, said system including a fluoroscopic simulator for generating a fluoroscopic image of a patient and comprising:
   cutter means;
   computer means for digitized processing of said image and control of said system, said computer means including image grabbing means for grabbing and processing said fluoroscopic image to convert said fluoroscopic image to a computer-handleable image to further process said image and, to generate cutter control signals;
   means for delivering said cutter control signals to said cutter means, said cutter means being operative in response to said cutter control signals for cutting a blocker or blocker pattern corresponding to said image; and,
   wherein said blocker pattern has a radiation opaquing material applied thereto so that said blocker pattern is at least partially radiation opaque.

9. The system of claim 8 wherein said blocker pattern is comprised of styrofoam.

10. The system of claim 9 wherein said opaquing material includes barium.

11. The system of claim 8 wherein said opaquing material includes barium.

12. The system of claim 1 wherein said computer means includes image linearization means for linearizing said image and image enhancement means for enhancing said image.

13. A radiation blocker for permitting radiation to reach a selected portion of a patient's anatomy, but for selectively blocking radiation from reaching surrounding tissue, said radiation blocker comprising:
 a cuttable material for having an opening cut therein in a contour corresponding to the portion of the patient's anatomy to be irradiated; and,
 a radiation opaquing material applied to said cuttable material so that said cuttable material is at least partially radiation opaque.

14. The radiation blocker of claim 13 wherein said radiation blocker is comprised of styrofoam.

15. The radiation blocker of claim 14 wherein said opaquing material includes barium.

16. The radiation blocker of claim 13 wherein said opaquing material includes barium.

17. A cutter for cutting a radiation blocker, said cutter comprising:
 a carriage for holding a blank into which a contour is to be cut corresponding to a portion of a patient's anatomy that is to be irradiated;
 guide means;
 a laser cutter mounted on said guide means and adjacent said blank;
 two-axis positioning means for selectively moving said guide means and thereby said laser cutter;
 means for generating electrical signals representative of the portion of said patient's anatomy that is to be irradiated; and,
 means for delivering said signals to said two-axis positioning means, said two-axis positioning means being operative in response to said signals to move said laser cutter for cutting said blank in a contour corresponding to the portion of said patient's anatomy that is to be irradiated.

18. A system for generating a radiation blocker, said system including a fluoroscopic simulator for generating a fluoroscopic image of a patient and comprising:
 aperture control means including a plurality of individually adjustable leaves for defining an aperture thereof;
 computer means for digitized processing of said image and control of said system, said computer means including image grabbing means for grabbing and processing said fluoroscopic image to convert said fluoroscopic image to a computer-handleable image, to further process said image and, to generate leaf control signals;
 means for delivering said leaf control signals to said aperture control means, said aperture control means being operative in response to said leaf control signals for selectively adjusting said leaves to form an aperture corresponding to said image.

19. A method of generating a radiation blocker comprising the steps of:
 generating a fluoroscopic image of a selected portion of a patient's anatomy;
 grabbing said fluroscopic image and digitizing and processing said image;
 displaying said images on a display apparatus;
 generating a blocker contour corresponding to selected portions of said displayed image and generating blocker contour signals corresponding to said blocker contour;
 delivering said blocker contour signals to a cutter; and,
 cutting a blank in response to said blocker contour signals so that said blank has cut therein a contour corresponding to said selected portion of said image.

20. The method of claim 19 wherein said cutting step includes cutting said blank with a heated wire cutter.

21. The method of claim 20 wherein said cutting step includes cutting said blank with a laser cutter.

22. A method of generating a radiation blocker, said method being used to control a plurality of individually adjustable leaves for defining an aperture in an aperture control means and comprising the steps of:
 generating a fluoroscopic image of a selected portion of a patient's anatomy;
 grabbing said fluroscopic image and digitizing and processing said image;
 displaying said image on a display apparatus;
 generating a blocker contour corresponding to selected portions of said displayed image and generating blocker contour signals corresponding to said blocker contour;
 delivering said blocker contour signals to said aperture control means; and,
 operating said aperture control means in response to said blocker contour signals so that the said leaves are selectively adjusted to form an aperture corresponding to said selected portion of said displayed image.

23. The method of claim 22 including the step of directing radiation through said aperture and toward the selected portion of the patient's anatomy that is to be irradiated.

24. A system for generating radiation blockers, said system including a fluoroscopic simulator for generating fluoroscopic images of a patient and comprising:
 cutter means;
 computer means for digitized processing of said images and control of said system, said computer means including image grabbing means for grabbing and processing said fluoroscopic images to convert said fluoroscopic images to computer-handleable images to further process said images, said computer means including image linearization means for linearization of said fluoroscopic images, image enhancing means for enhancing said fluoroscopic images, and image composing means for composing a plurality of said fluoroscopic images into a composite image, said fluoroscopic images being overlapping images that are offset with respect to one another, said computer means including contour image acquisition means for acquisition of a contour image and superpositioning means for superpositioning said contour image upon said composite image, and said computer means including means to generate cutter control signals;
 means for delivering said cutter control signals to said cutter means, said cutter means being operative in response to said cutter control signals for cutting a blocker paragon corresponding to said contour image; and
 verification means for verification of said blocker paragon, said verification means including projection means for projecting said blocker paragon's silhouette.

25. A system according to claim 24, wherein said cutter means is a heated-wire cutter comprising a two-axis positioner for positioning a heated wire during cutting.

26. A system according to claim 24, wherein said cutter means is a laser cutter comprising a two-axis positioner for positioning of a laser beam during cutting.

27. A system according to claim 24, wherein said cutter means is a milling apparatus comprising a positioner having five degrees of freedom for positioning a milling cutter during cutting.

28. A system according to claim 24, including blanks for said blocker paragons, said blanks being comprised of material that has a radiation opaque material applied thereto so that said blocker paragon is at least partially radiation opaque.

29. A system according to claim 24, wherein said blocker paragon has a radiation opaque material applied thereto so that said blocker paragon is at least partially radiation opaque.

30. A system according to claim 24, including blanks for said blocker paragons, said blanks being comprised of radiation opaque material so that said blocker paragon is at least partially transparent to radiation through selected regions thereof.

31. A system according to claim 24, wherein said blocker paragon comprises a pattern or mold for casting of radiation opaque material therein for the fabrication of a blocker.

32. The system according to claim 31, wherein said pattern or mold is cut by said cutter means to a depth that is less than the thickness of said pattern or mold.

33. A system according to claim 24, wherein said computer means includes compensator information acquisition means for acquisition of compensator information, said compensator information acquisition means including means for processing said information to generate compensator cutter control signals, said computer means including means for delivering said compensator cutter control signals to said cutter means so that said cutter means is operative in response to said compensator cutter control signals for cutting a compensator filter corresponding to said compensator information.

34. The system according to claim 33, wherein said computer means includes means for combining and delivering combination signals of said cutter control signals for cutting said blocker paragon and said compensator cutter control signals, said combination signals being delivered to said cutter means, said cutter means being operative in response to said combination signals for cutting a combination blocker/compensator.

35. A system according to claim 24, wherein said computer means includes compensator information acquisition means for acquisition of compensator information, said compensator information acquisition means including means for processing said information to generate compensator cutter control signals, said computer means including means for delivering said compensator cutter control signals to said cutter means so that said cutter means is operative in response to said compensator cutter control signals for cutting a compensator mold for casting of radiation attenuating material therein for the fabrication of a compensator filter corresponding to said compensator information.

36. The system according to claim 35, wherein said computer means includes means for combining and delivering combination signals of said cutter control signals for cutting said blocker paragon and said compensator cutter control signals, said combination signals being delivered to said cutter means, said cutter means being operative in response to said combination signals for cutting a combination blocker/compensator mold for casting of radiation attenuating material therein for the fabrication of a combination blocker/compensator filter.

37. A method of generating a radiation blocker comprising the steps of:
generating a plurality of fluoroscopic images of portions of a patient's anatomy, said fluoroscopic images being overlapping images that are offset with respect to one another;
grabbing said fluoroscopic images and digitizing and processing said fluoroscopic images;
linearizing and enhancing said fluoroscopic images;
composing said plurality of fluoroscopic images into a composite image;
displaying said composite image on a display apparatus;
superposing and displaying a contour image upon said composite image;
generating signals corresponding to said contour image;
delivering said signals to a fabricating means;
fabricating by said fabricating means in response to said signals a blocker paragon corresponding to said contour image; and
verifying said blocker paragon by projecting said blocker paragon's silhouette.

38. The method of claim 37 wherein said fabricating step includes cutting said blocker paragon with a heated wire cutter.

39. The method of claim 37 wherein said fabricating step includes cutting said blocker paragon with a laser cutter.

40. The method of claim 37 wherein said fabricating step includes cutting said blocker paragon with a milling cutter.

41. The method of claim 37 wherein said fabricating step includes the step of fabricating said blocker paragon by cutting a pattern or mold.

42. The method of claim 41 wherein said step of cutting is limited to cutting to a depth that is less than the thickness of said pattern or mold.

43. The method of claim 37 including the steps of:
acquiring compensator filter information;
generating signals corresponding to said compensator filter information;
delivering said signals to said fabricating means; and
fabricating a compensator filter by said fabricating means in accordance with said compensator filter information.

44. The method of claim 43 including the steps of:
combining said signals corresponding to said contour image with said signals corresponding to said compensator filter information into combination signals;
delivering said combination signals to said fabricating means;
fabricating a combination blocker/compensator filter mold by said fabricating means in response to and in accordance with said combination signals; and
casting a combination blocker/compensator filter in said mold.

45. The method of claim 43 including the steps of:
combining said signals corresponding to said contour image with said signals corresponding to said compensator filter information into combination signals;
delivering said combination signals to said fabricating means; and
fabricating a combination blocker/compensator in said fabricating means by milling of a radiation attenuating material blank in response to and in accordance with said combination signals.

* * * * *